United States Patent
Woias et al.

[19]

[11] Patent Number: 6,129,702
[45] Date of Patent: Oct. 10, 2000

[54] MEDICAMENT DOSING SYSTEM

[75] Inventors: Peter Woias; Martin Richter, both of München, Germany

[73] Assignee: Fraunhofer-Gesellschaft zur Forderung angewandten Forschung e.V., Munich, Germany

[21] Appl. No.: 09/319,291

[22] PCT Filed: Nov. 25, 1997

[86] PCT No.: PCT/EP97/06574

§ 371 Date: Jun. 6, 1999

§ 102(e) Date: Jun. 6, 1999

[87] PCT Pub. No.: WO98/24496

PCT Pub. Date: Jun. 11, 1998

[30] Foreign Application Priority Data

Dec. 3, 1996 [DE] Germany .......................... 196 50 115

[51] Int. Cl.[7] .................................................. A61M 31/00
[52] U.S. Cl. ........................ 604/65; 604/250; 604/34
[58] Field of Search .............................. 604/19, 48, 65, 604/67, 246, 247, 250, 27, 30, 34, 118, 131, 151, 153

[56] References Cited

U.S. PATENT DOCUMENTS

| 5,377,524 | 1/1995 | Wise et al. |
| 5,515,735 | 5/1996 | Sarihan . |

FOREIGN PATENT DOCUMENTS

| 0435237 | 7/1991 | European Pat. Off. |
| 3814150 | 4/1988 | Germany . |
| 382744A1 | 8/1988 | Germany . |
| 285188 | 6/1989 | Germany . |
| 19501691 | 1/1995 | Germany . |
| 05157599 | 6/1993 | Japan . |
| 8605993 | 10/1986 | WIPO . |
| 9632975 | 10/1996 | WIPO . |

OTHER PUBLICATIONS

R. Werthschützky, "Application of Silicon Sensors in Process Measuring Devices for Pressure Measurements—Current Status and Coming Opportunities", Sep. 1992, No. 9, Munchen, DE.

Oosterbroek et al., "Designing, Realization and Characterization of a Novel Capacitive Pressure/Flow Sensor", Jun. 16–19, 1997, 1997 International conference of Solid–State Sensors and Actuators.

Boillat, et al., "A Differential Pressure Liquid Flow Sensor for Flow Regulation and Dosing Systems", 1995, IEEE.

*Primary Examiner*—Sharon Kennedy
*Assistant Examiner*—Deborah Blyveis
*Attorney, Agent, or Firm*—Beyer Weaver & Thomas, LLP

[57] ABSTRACT

A medicament dosing system comprises a replaceable unit and a permanent unit. The replaceable unit comprises a fluid reservoir for receiving therein a pressurizable liquid medicament, a temperature sensor for detecting the temperature of said liquid medicament, a fluid channel which is provided with a flow resistor and which is in flow communication with the fluid reservoir, and a hose means which is connected to the fluid channel. The permanent unit comprises a squeezing valve means for squeezing the hose means together, and a control means which is coupled to the temperature sensor and the squeezing valve means so as to control a flow rate of the liquid medicament by clocked actuation of said squeezing valve means depending on the temperature detected. Alternatively, the temperatur sensor can be arranged in the permanent unit.

18 Claims, 7 Drawing Sheets

FIG.3B CROSS-SECTION A-A

MEDICAMENT DOSING SYSTEM

BACKGROUND OF THE INVENTION

1. Field of the Invention

The present invention relates to a medicament dosing system and, in particular, to a medicament dosing system operating according to the overpressure principle.

2. Description of Prior Art

Lately, medicament dosage is carried out predominantly by dosing systems operating according to the overpressure principle. A schematic representation illustrating the overpressure principle is shown in FIG. 8. Such systems consist of a fluid reservoir 10 and of a flow resistor 12 arranged e.g. on or in a fluid line 14 connected to the fluid reservoir 10. A pressure transmitter means 16 serves to apply pressure to the liquid medicament contained in the fluid reservoir 10. The pressure transmitter means produces a pressure p, whereby the fluid reservoir 10 is acted upon by a specific overpressure $P_1$ relative to the pressure $p_0$ at the outlet of the flow resistor 12. The pressure $p_1$ substantially corresponds to the pressure p produced by the pressure transmitter means 16. When the system is in operation, a flow Q is caused by the differential pressure applied to the flow resistor 12.

For a circular cross-section of the flow resistor, the magnitude of the flow Q can be calculated according to the known Hagen-Poiseuille law:

$$Q = \frac{\pi \cdot \Delta p \cdot R^4}{8 n_v L}$$

The flow rate Q is determined by the following influencing quantities:
- the viscosity $n_v$ of the medium,
- the effective flow cross-section $\pi R^4/8$ and the length L of the flow resistor,
- the differential pressure $\Delta p$ between the inlet and the outlet of the flow resistor, and
- the temperature as an indirect influencing quantity, e.g. by the temperature-dependent viscosity of the fluid.

For other flow cross-sections, analogous rules can be determined which differ from the rule mentioned in the above equation substantially with regard to the taking into account of the effective flow cross-section of the flow resistor. Such analogous rules e.g. for micromechanically produced flow resistors are described in "Micro Channels for Applications in Liquid Dosing and Flow Rate Measurement" M. Richter, P. Woias, D. Weiß, Proceedings of Euro Sensors X, Sep. 8 to 11, 1996, Leuven, Belgium, Vol. 4, pp. 1297 to 1300.

The technical embodiments of existing dosing systems vary greatly and use in a great variety of combinations mechanisms like mechanical systems, e.g. spring-pressure systems, electrochemical systems, e.g. electrolytic cells, thermopneumatic systems, e.g. the evaporation pressure of a highly volatile substance, and the gravitational force. The elements used as flow resistor are normally plastic capillaries, glass capillaries and metal capillaries.

According to the above equation, the radius R influences the flow rate Q through the term $R^4$ to the fourth power, when the flow resistor is circular in cross-section. This means that, for achieving exact dosage, flow resistors having a high geometrical accuracy must be realized. Such an accuracy is only possible on the basis of a comparatively high technical expenditure. Simple systems including plastic capillaries are additionally disadvantageous insofar as the capillary stretches depending on the pressure applied, whereby the dosing accuracy will decrease.

In addition, comparable micromechanical embodiments used for glucose measurements by means of a microdialysis are known. In such a micromechanical embodiment, a microcapillary for flow adjustment is realized on a silicon chip together with glucose sensors. This known set-up is, however, not used for medicament dosage, but it uses the above-described over-pressure principle only for adjusting the flow rate of the carrier medium for the microdialysis.

A further known implementable micromechanical dosing system uses a solvent reservoir as a constant pressure transmitter and an array of micromechanically realized flow resistors for flow rate adjustment. The geometry of the whole flow path is varied by coupling and decoupling individual microflow resistors via respective microvalves associated therewith, whereby a dosing rate variation switched in steps is achieved. For measuring the flow, pressure sensors located at various points of the array are used. Such a system with an array of microflow restrictions does not permit a continuous adjustment of the dosing rate, the technical expenditure being, in addition, very high, since several microvalves and pressure sensors are necessary; hence, such a system can only be used in a limited field of application for reasons of costs.

The majority of the known dosing systems cannot be influenced from outside, i.e. the flow rate cannot be varied when the system is in operation, such varying being e.g. necessary for automatically observing a circadian rhythm when dosing a medicament. In addition, the influence of the temperature on the viscosity of the fluid and, consequently, on the dosing rate is normally not compensated in known dosing systems. Especially in the case of portable dosing systems, this may result in considerable dosing errors. When the flow rates to be adjusted are very low, $\mu$l/min to pl/min, flow resistors with effective cross-sectional dimensions in the $\mu$m range are required. Such cross-sectional dimensions cannot be produced by conventional techniques. Known dosing systems which do not use any complicated components as disposable components do not permit any continuous adjustment of the dosing rate.

DE-A-19501691 describes an non-invasive system for fluid flow supervision in which the infusion rate is adjusted by pulsed control of a fluid feed pump. The temperature of the fluid fed is supervised by a temperature sensor.

In DE-A-3827444 a method and a device for detecting a fluid flow in a line are described. The known device comprises a heating means attached to said line and two temperature sensors attached to said line upstream and downstream of said heating means. The temperatures measured at the temperature sensors serve to make statements on the existence of a flow, the direction of flow as well as the flow velocity.

SUMMARY OF THE INVENTION

It is the object of the present invention to provide medicament dosing systems which permit a continuous adjustment of the dosing rate and which, in addition, do not comprise any expensive disposable components.

In accordance with a first aspect of the present invention, this object is achieved by a medicament dosing system comprising a replaceable unit and a permanent unit, the replaceable unit having the following features:
- a fluid reservoir for receiving therein a pressurizable liquid medicament;
- a temperature sensor for detecting the temperature of said liquid medicament;

a fluid channel which is provided with a flow resistor and which is in flow communication with the fluid reservoir; and a hose means which is connected to the fluid channel; and the permanent unit having the following features:

a squeezing valve means for squeezing the hose means together; and a control means which is coupled to the temperature sensor and the squeezing valve means so as to control a flow rate of the liquid medicament by clocked actuation of said squeezing valve means depending on the temperature detected.

In accordance with a second aspect of the present invention, this object is achieved by a medicament dosing system comprising a replaceable unit and a permanent unit, the replaceable unit having the following features:

a fluid reservoir for receiving therein a pressurizable liquid medicament;

a fluid channel which is provided with a flow resistor and which is in flow communication with the fluid reservoir; and a hose means which is connected to the fluid channel; and the permanent unit having the following features:

a temperature sensor for detecting the temperature of said liquid medicament;

a squeezing valve means for squeezing the hose means together; and a control means which is coupled to the temperature sensor and the squeezing valve means so as to control a flow rate of the liquid medicament by clocked actuation of said squeezing valve means depending on the temperature detected.

The liquid medicament contained in the fluid reservoir preferably has a pressure applied thereto by means of a pressure transmitter; furthermore, the medicament dosing system according to the present invention can comprise at least one pressure sensor for detecting the pressure of the liquid medicament before the flow resistor. In addition, the medicament dosing system according to the present invention can comprise a further pressure sensor after the flow resistor, the control means controlling the flow rate of the liquid medicament depending on the temperature detected and the difference between the pressures detected.

The dosing system according to the present invention operates according to the overpressure principle and uses preferably a micromechanically produced flow resistor, and it offers possibilities of externally influencing the dosing rate via the control device and for the purpose of compensating temperature effects.

The medicament dosing system according to the present invention uses a squeezing valve, which is clock-controlled by the control means, so as to permit or prevent a flow through the hose. This squeezing valve engages the hose from outside and squeezes it together so as to prevent the liquid medicament from flowing through. Hence, the valve does not come into contact with the medicament. The valve can therefore be part of the permanent device. It follows that the disposable unit of the medicament dosing system according to the present invention only comprises the preferably micromechanically produced components of the fluid reservoir and of the fluid channel, which is connected to said fluid reservoir and provided with a flow resistor, and the optionally integrated pressure sensors as well as the hose which is connected to the fluid channel. In one embodiment, the disposable unit additionally comprises the temperature sensor. It follows that the present invention is advantageous in comparison with known dosing systems insofar as it does not include any expensive disposable components.

The medicament dosing system according to the present invention permits a continuous adjustment of the dosing rate, the disposable components used being not more expensive than those used in the previous known prior art. The system according to the present invention is based on the already known principle of overpressure dosage using e.g. constant pressure transmitters and, consequently, it permits a further development of already existing systems for achieving improved properties. The structural design of the components used permits a throw-away operation due to lower production costs in combination with an improved functionality, e.g. lower dosing rates, a higher production accuracy and, consequently, less expenditure, and it permits, due to the fact that only micromechanical components are used in the sterile region, a repeated use with intermediate sterilization, if necessary. The system according to the present invention can be used for home-care operation alone, for throw-away operation as well as for clinic operation with repeated use.

BRIEF DESCRIPTION OF THE DRAWINGS

In the following, preferred embodiments of the present invention will be explained in more detail making reference to the drawings enclosed, in which

FIGS. 3A to 3C show schematic representations of a micromechanically produced flow resistor which is adapted to be used in the medicament dosing system according to the present invention;

DESCRIPTION OF PREFERRED EMBODIMENTS OF THE INVENTION

Figure 1:
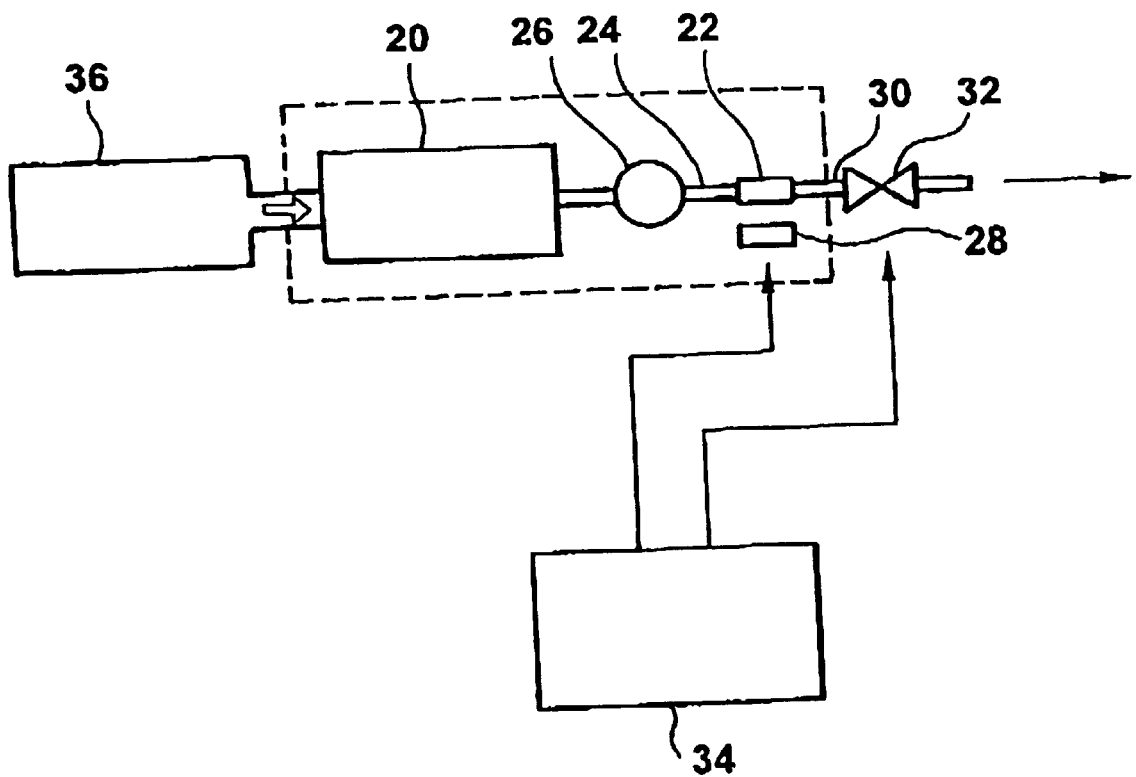
FIG. 1 shows a schematic representation of a medicament dosing system according to the present invention.

Making reference to FIG. 1 and 2, a preferred embodiment of the medicament dosing system according to the present invention will be described in the following. The system comprises a fluid reservoir 20 and a flow resistor 22, which is in fluid communication with said fluid reservoir 20, e.g. via a fluid line 24. In the embodiment shown, a filter 26 is optionally arranged between the fluid reservoir 20 and the flow resistor 22. The filter 26 can be used for filtering air bubbles and/or for filtering bacteria. A temperature sensor 28 for detecting the temperature of the liquid medicament is arranged preferably in the area of the flow resistor 22. The components shown in FIG. 1 within the dashed frame represent the replaceable parts of the medicament dosing system according to the present invention, i.e. the disposable components. Alternatively, the temperature sensor can be arranged in the medicament dosing system in such a way that it is able to detect the temperature of the liquid medicament; in this case, it is, however, not associated with the disposable component.

The outlet of the flow resistor 22 is in fluid communication with a flexible hose means 30. The hose means 30 can be squeezed together by a squeezing valve 32 by actuating said valve, and, when the squeezing valve 32 is not actuated, it is open for fluid passing therethrough. A control unit 34 is electrically coupled to the temperature sensor 28 and the squeezing valve 32.

In FIG. 1 a pressure transmitter 36 is additionally shown schematically, said pressure transmitter applying pressure to a liquid medicament contained in the fluid reservoir 20. The pressure transmitter 36 can e.g. be a constant pressure transmitter having an arbitrary known structural design. The systems used as a pressure transmitter can, for example, be mechanical systems, electrochemical systems or thermopneumatic systems. In addition, it is also possible to use the gravitational force for pressurizing the liquid medicament. Alternatively, the pressure transmitter can consist of the border of the fluid reservoir, provided that said border is implemented such that it is capable of contracting elastically, or of a gas which is present in the fluid reservoir in addition to the liquid medicament and which therefore applies pressure to said liquid medicament.

The control means 34 is preferably provided with a data interface, a microcontroller as well a display device, e.g. a screen, and an input device, e.g. a keyboard.

As has been explained hereinbefore with regard to the prior art, the flow rate through a flow resistor depends on the viscosity of the medium, the effective flow cross-section and the length of the flow resistor, and the differential pressure between the inlet and the outlet of the flow resistor. The dependence of the flow on these values for specific flow cross-sections is explained in the above-mentioned publication "Micro Channels for Applications in Liquid Dosing and Flow Rate Measurement".

In the case of a given cross-section of the flow resistor, the flow rate therefore depends on the differential pressure and the temperature of the medium, since the viscosity of the medium varies strongly with the temperature of said medium. It follows that, at a given constant pressure, which is supplied by the pressure transmitter 36, the flow rate depends exclusively on the temperature of the medium. The control unit 34 detects this temperature and clocks the control valve in such a way that a desired flow rate is obtained for the temperature detected.

The microflow resistor is preferably dimensioned such that, at the lowest imaginable operating temperature $T_{target}$, the desired target flow is maintained during continuous operation, i.e. when the squeezing valve 32 is constantly open. As soon as the temperature exceeds this value, dosing is no longer carried out continuously, but with the aid of the squeezing valve 32 in an ON/OFF alternating operation.

Depending on the temperature detected and on a viscosity/temperature curve, which is preferably stored in a memory of the control means 34, as well as on the basis of the above-explained correlation between the flow rate and the physical parameters of the flow resistor and of the medium, the control means 34 determines the pulse/pause ratio such that the effective dosing rate, i.e. the product of flow rate and pulse duty ratio, is kept constant.

Figure 2:
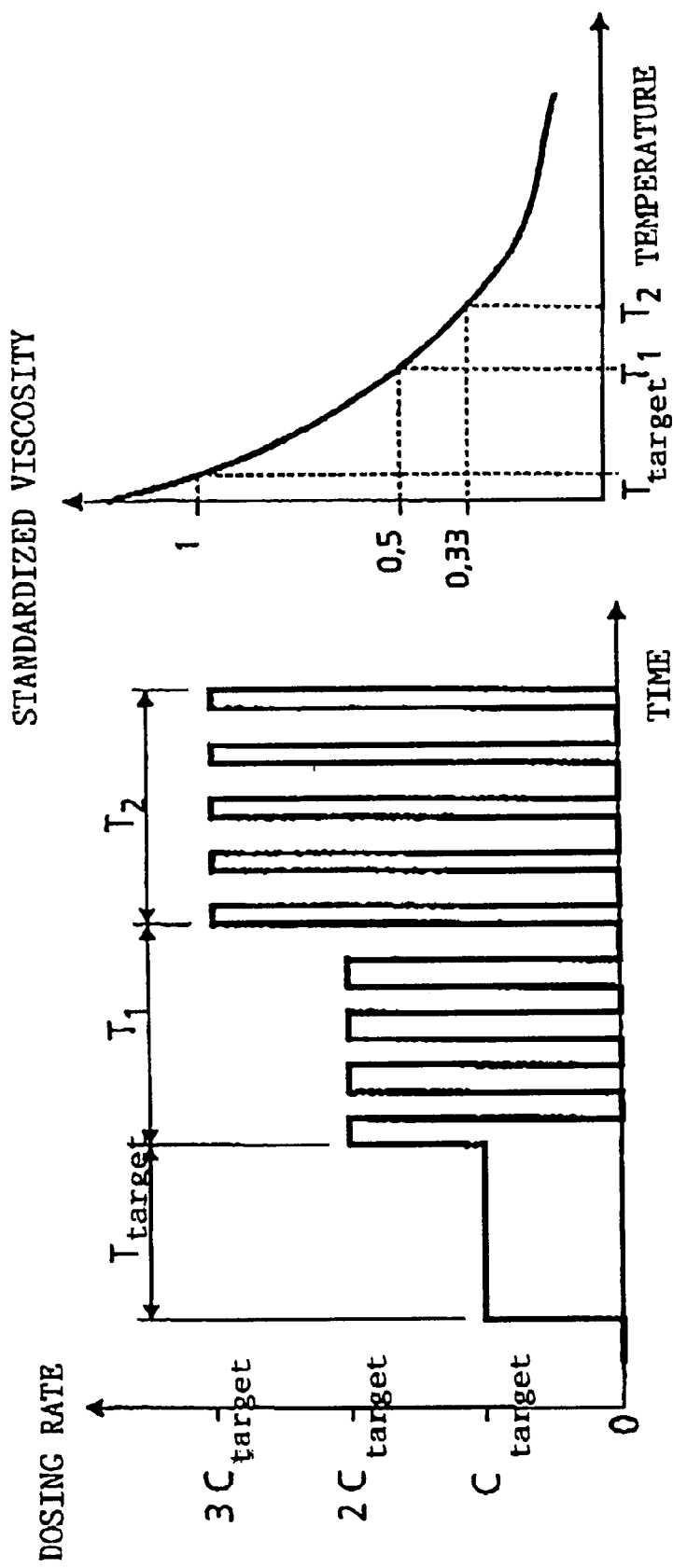
FIG. 2 shows diagrams for illustrating the mode of operation of the medicament dosing system according to the present invention.

A schematic representation of this control method is shown in FIG. 2. In the right part of FIG. 2, the standardized viscosity of a medium to be transported is plotted against the temperature. At the temperature $T_{target}$, the standardized viscosity is 1, whereas the viscosity decreases as the temperature increases, at $T_1$ to 0.5 and at $T_2$ to 0.33.

As has been explained hereinbefore, the flow resistor is dimensioned such that, at the lowest imaginable operating temperature $T_{target}$, the desired target flow $C_{target}$ is maintained in continuous operation, i.e. without clocked actuation of the squeezing valve. When the temperature increases to $T_1$, at which the flow rate through the flow resistor is twice as high as the flow rate at temperature $T_{target}$, the squeezing valve is clocked such that it is only open half the time. This results in a total flow of $C_{target}$.

When the temperature increases still further to $T_2$, the flow rate through the flow resistor will be $3 \cdot C_{target}$ at constant pressure. Hence, the squeezing valve will be clocked such that the valve will remain closed two thirds of the time and be open one third of the time. Due to the fact that the closed-time of the squeezing valve is twice as long as the open-time of said squeezing valve, in which a flow of $3 \cdot C_{target}$ flows through the flow resistor, a total flow of $C_{target}$ is again obtained.

A temporally variable dosing rate can be realized by additionally influencing the pulse/pause ratio. In addition, the flow can be switched off completely with the aid of the squeezing valve. In the event of a malfunction where the outlet pressure exceeds the maximum pressure range of the pressure transmitter, this valve will prevent a return flow into the fluid reservoir and a possibly occurring diffusion of fluid from the reservoir.

For improving the adjustment accuracy of the flow rate and for implementing a dosage supervising function which detects automatically whether there is a flow of medicaments and, if so, the magnitude of said flow of medicaments, the medicament dosing system according to the present invention can additionally be provided with a pressure sensor which is arranged before the flow resistor for detecting the pressure acting on the liquid medicament. It is then not the value of the constant pressure, which is supplied by the pressure transmitter, but the value of the pressure which is detected by the pressure sensor that is used for controlling the pulse/pause ratio for adjusting the flow rate. Pressure fluctuations, which may be caused by the pressure transmitter or by other system parameters, can be compensated for in this way. Alternatively to one pressure sensor, the system may also comprise two pressure sensors, one of said pressure sensors being arranged before the flow resistor, whereas the other pressure sensor is arranged behind said flow resistor. Instead of the pressure value supplied by the constant pressure transmitter, the pressure difference between the inlet of the flow resistor and the outlet of the flow resistor is then used for determining the pulse/pause ratio via the correlation between the flow rate and the viscosity of the medium, the effective flow cross-section and the length of the flow resistor as well as the pressure acting on the medium.

Figure 3A:
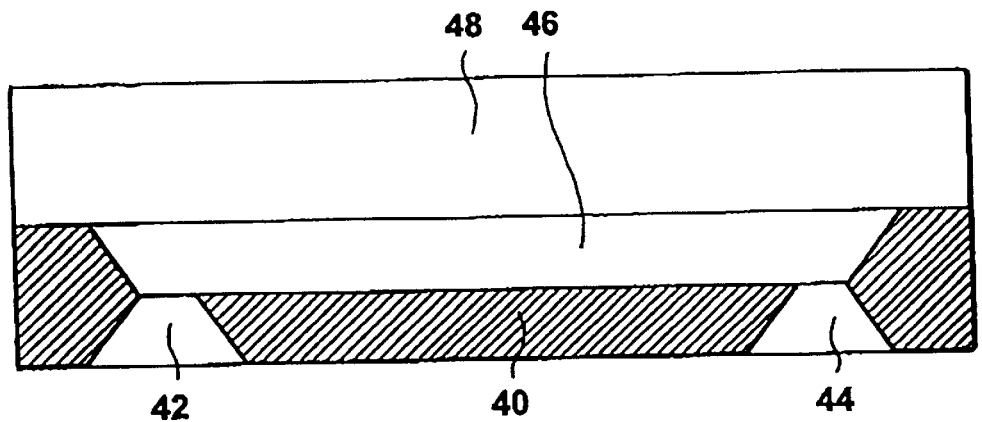

FIG. 3A shows an embodiment of a micromechanically formed flow resistor which is adapted to be used for the present invention. In a main surface of the substrate 40, an inlet opening 42 and an outlet opening 44 are formed. In the other main surface of the substrate 40 a flow channel 46 is formed in such a way that the inlet opening 42 and the outlet opening 44 are in fluid communication with said flow channel 46. The inlet and the outlet opening are realized as planar structures in the substrate. The substrate 40 can, for example, be a semiconductor chip, e.g. a silicon chip, in which arbitrary cross-sections and arrangements, e.g. a meandrous shape, of the channel are formed with due regard to the desired flow resistance; for this purpose, arbitrary wet-chemical methods, e.g. KOH etching, or dry-chemical methods, e.g. plasma etching, can be used. Alternatively, the substrate 40 can be a plastic substrate produced by means of known micromechanical injection methods.

A cover 48 is attached to the surface of the substrate 40 in which the channel 46 is formed. The cover 48 and the recess 46 in the substrate 40 define the cross-section of the flow resistor. The cover can, for example, be a glass top applied by means of an anodic bonding method. Alternatively, a further semiconductor substrate, e.g. of silicon, can be used as a cover 48.

Figure 3C:
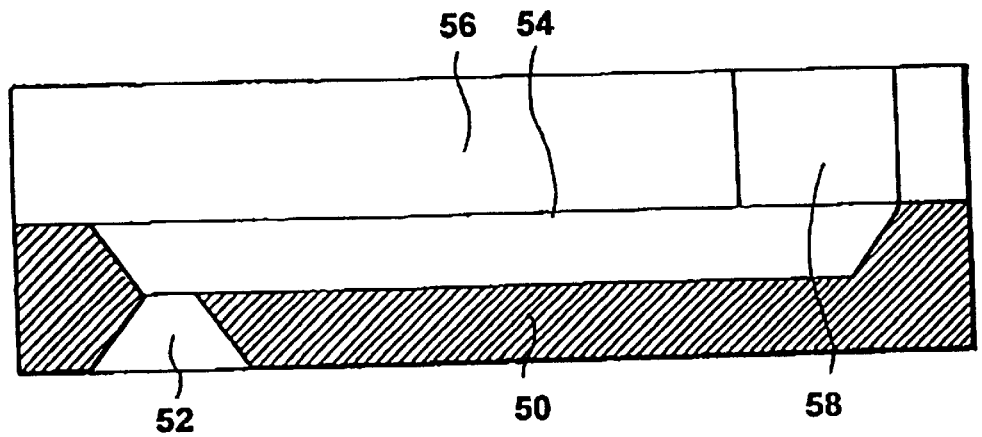
Figure 3C:
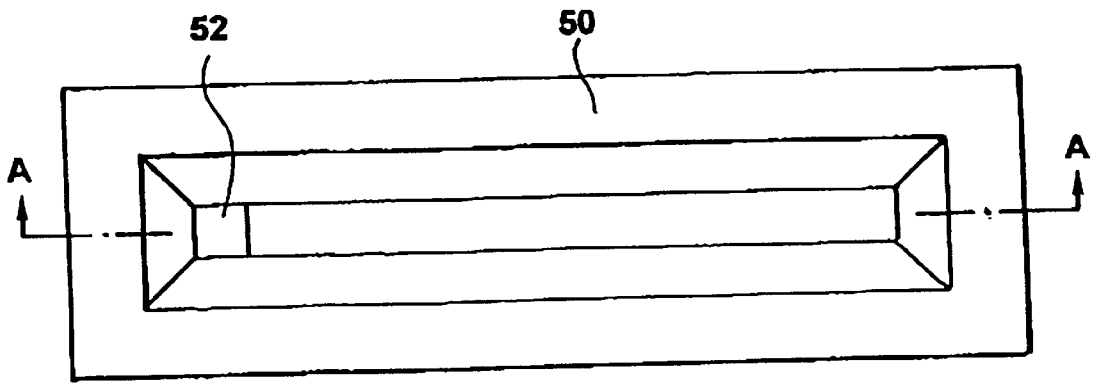

FIGS. 3B and 3C show a sectional view and a top view, without cover, of a further embodiment of a micromechanically produced flow resistor. A substrate 50 has formed therein an inlet opening 52 and a flow channel 54. A cover 56 is again arranged on top of the flow channel 54. In this embodiment, the outlet opening 58 is, however, provided in the cover 56. The materials and the production methods of the substrate and of the cover can correspond to those of the embodiment described in connection with FIG. 3A.

FIG. 3C shows a top view of the sectional view shown in FIG. 3B, FIG. 3B representing a section along line A—A of FIG. 3C. The trapezoidal openings shown in the figures can be obtained by conventional etching methods. The dependency of the flow rate on such a trapezoidal cross-section is known in the field of technology, cf. the above-mentioned publication "Micro Channels for Applications and Liquid Dosing and Flow Rate Measurement".

The temperature sensor of the medicament dosing system according to the present invention is preferably integrated in the above-described micromechanical structure.

Figure 4A:
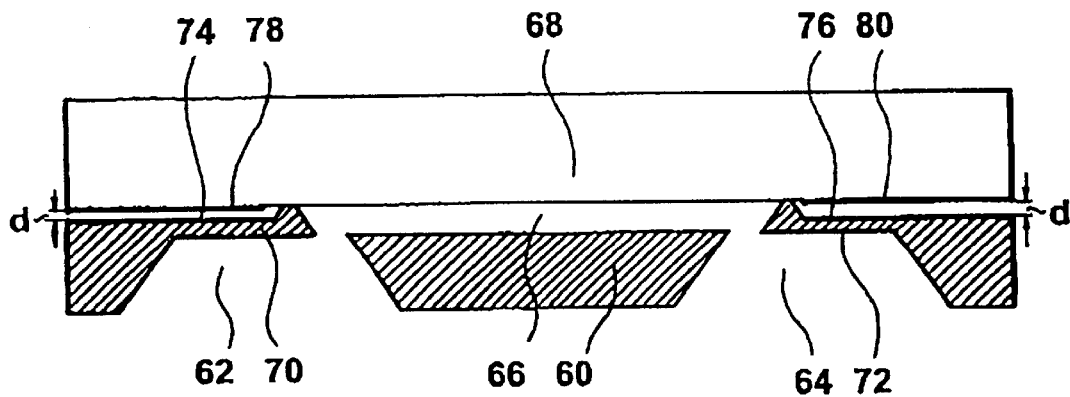
FIGS. 4A and 4B show a sectional view and a top view of an embodiment of a micromechanically produced flow resistor with integrated pressure sensors.
Figure 4B:
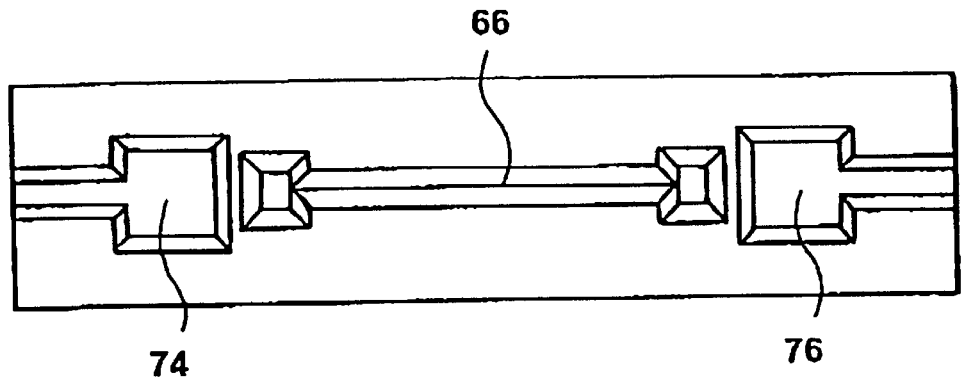

FIGS. 4A and 4B show a cross-sectional view and a top view of a further embodiment of a micromechanically produced flow resistor having pressure sensors integrated therein at the inlet and at the outlet of the flow resistor so as to permit a measurement of the differential pressure. A main surface of the substrate 60 has formed therein an inlet opening 62 and an outlet opening 64. The other main surface of the substrate 60 has formed therein a flow channel 66 which is in fluid communication with the inlet opening 62 and the outlet opening 64. The flow channel 66 defines together with a cover 68 the cross-section of the flow resistor.

The embodiment shown in FIGS. 4A and 4B additionally comprises two capacitive pressure sensors which are formed by membrane electrodes 74 and 76 arranged on membranes 70 and 72 and by electrodes 78 and 80 arranged on the cover in opposed relationship with said membrane electrodes. The membrane electrodes 74 and 76 are spaced from the counter-electrodes 78 and 80 by the distance d. The membrane electrode attached to the membrane deforms in response to pressure fluctuations, whereby the capacitance of the electrode arrangement as output signal is changed.

Figure 5:
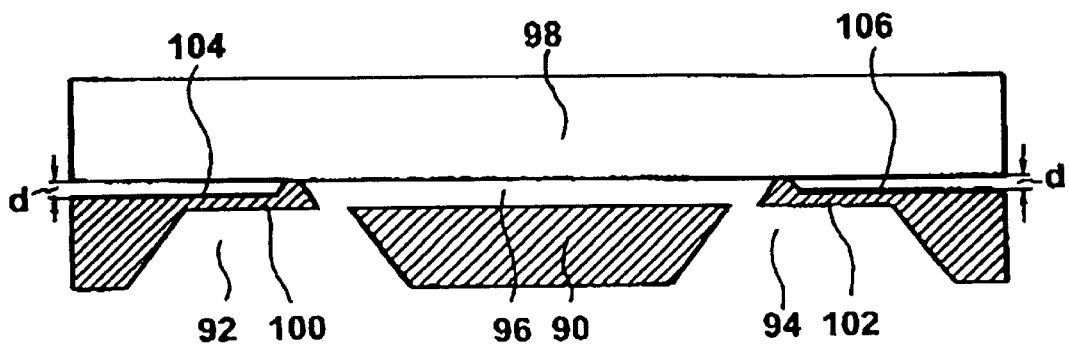
FIG. 5 shows a sectional view of a further embodiment of a micromechanically produced flow resistor with integrated pressure sensors.

FIG. 5 shows a further embodiment of a micromechanically produced flow resistor which can be used for the present invention. Different main surfaces of a substrate have again formed therein an inlet opening 92, an outlet opening 94 as well as a flow channel 96 in such a way that the inlet opening 92 and the outlet opening 94 are each in fluid communication with the flow channel 96. The upper side of the flow channel 96 is covered by a cover 98. Membranes 100 and 102 are again formed in the substrate 90, said membranes having piezoresistive resistors 104 and 106 integrated therein in the embodiment shown in FIG. 5. The value of the piezoresistive resistors 104 and 106 changes in dependence upon the mechanical deformation of the membrane and can be evaluated as a measurable variable for the pressure. The piezoresistive electrodes are spaced from the lower edge of the cover 98 by a motion distance d.

In addition to the above-described micromechanically formed flow resistors, also the fluid reservoir as well as the connection between said fluid reservoir and the flow resistor can be formed in a substrate in the medicament dosing system according to the present invention, preferably in the same substrate as the flow resistor. A substrate structured in this way can be accommodated in a housing so that a pressure transmitter as well as the hose means can be connected to the fluid reservoir and the flow resistor, respectively. An example of fluidic fittings for connecting micromechanically produced flow resistors, which fulfills compatibility requirements with already existing standards, is shown in FIG. 6.

Figure 6:
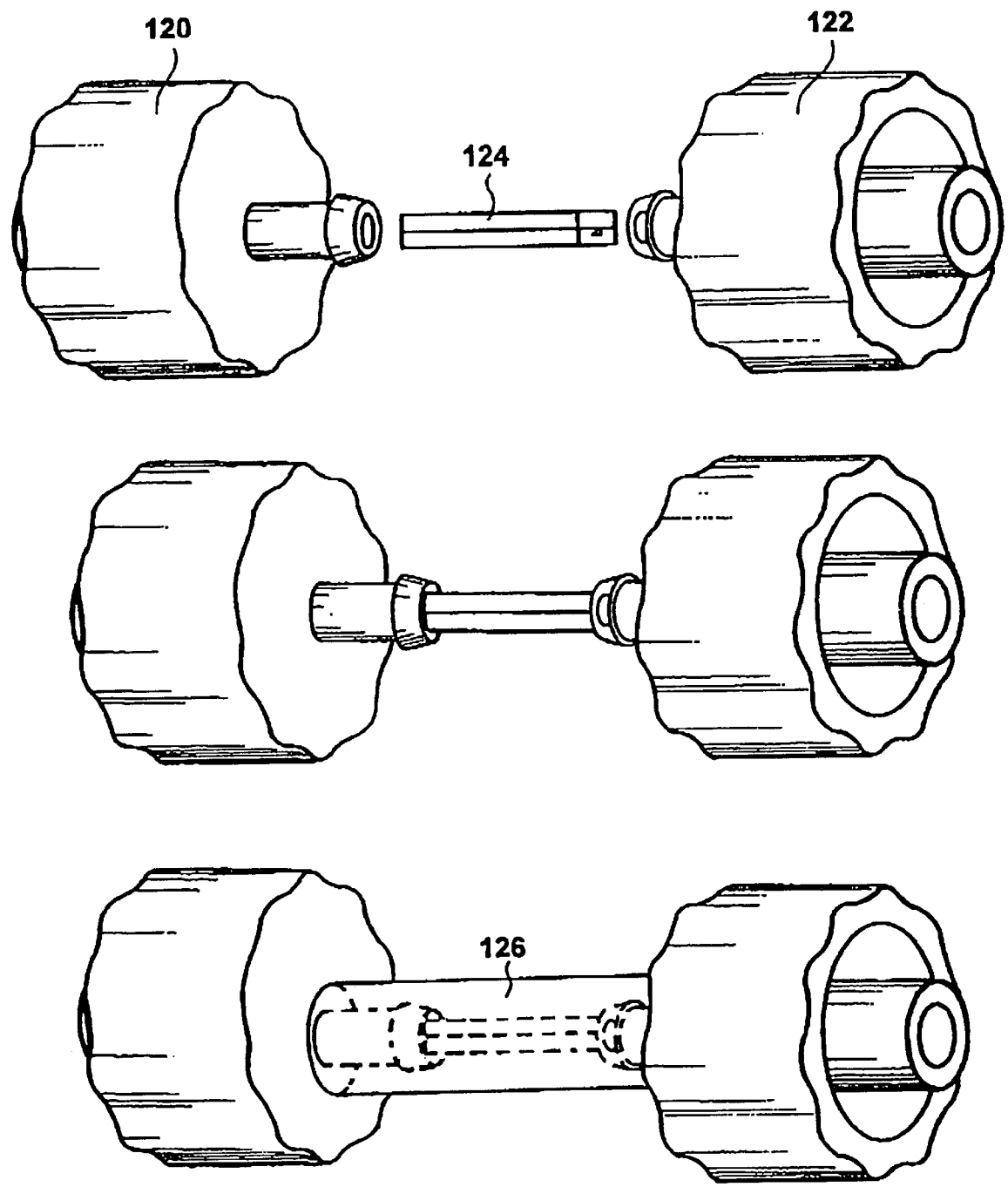
FIG. 6 shows a schematic representation of a so-called Luer system used for fluidically connecting micromechanically produced fluid systems.

The system shown in FIG. 6 is based on so-called Luer connectors. The Luer system shown in FIG. 6 is realized by a two-part housing comprising a first housing component 120 and a second housing component 122. The housing component 120 and the housing component 122 are provided with suitable connection elements and internal fluid channels matching the inlet and outlet geometry of the micromechanically produced fluid system. The micromechanically produced fluid system 124 is then attached to these inlet and outlet openings by means of a sealing mounting method. This attaching step can be carried out e.g. by glueing or by mounting with the aid of O-rings. Finally, an outer envelope 126 of the micromechanical fluid system can be provided. Such connection systems for micromechanically produced fluid conducting devices are known in the field of technology.

Figure 7A:
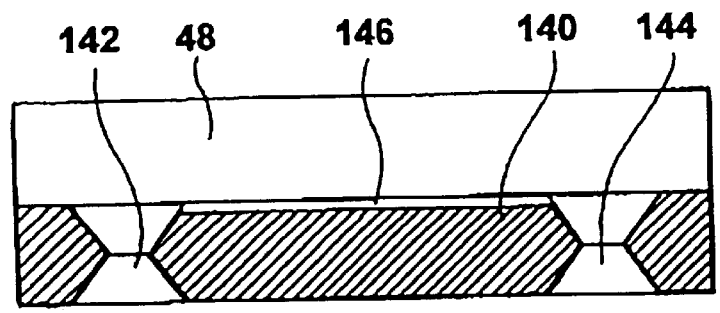
FIGS. 7A and 7B each show a cross-sectional view and a top view of further embodiments of micromechanically produced flow resistors.
Figure 7A:
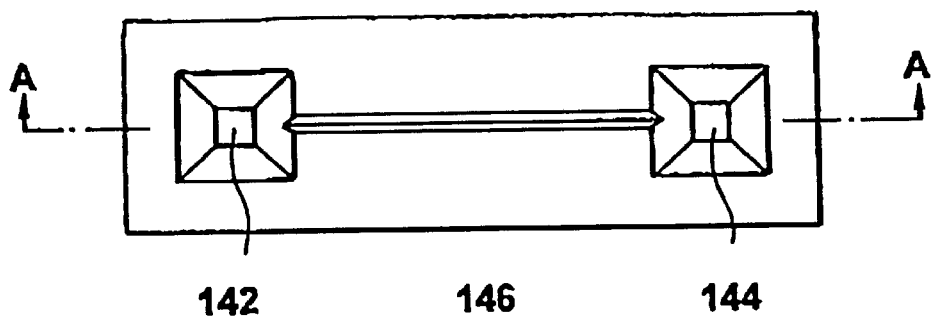
Figure 7B:
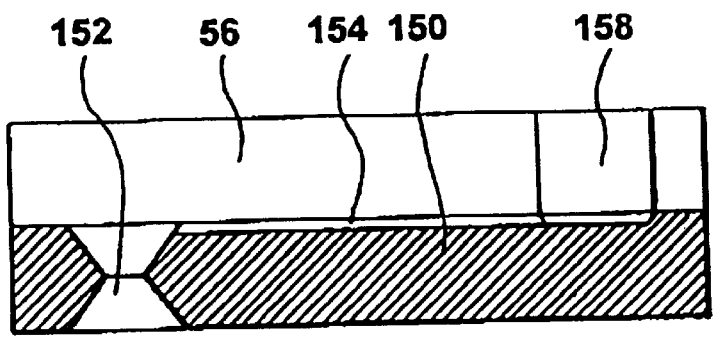
Figure 7B:
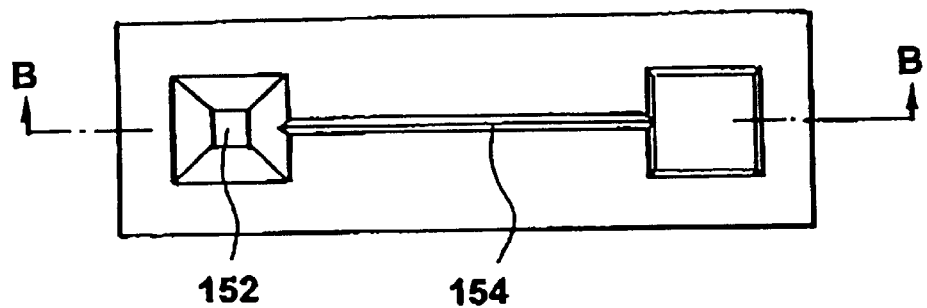
Figure 8:
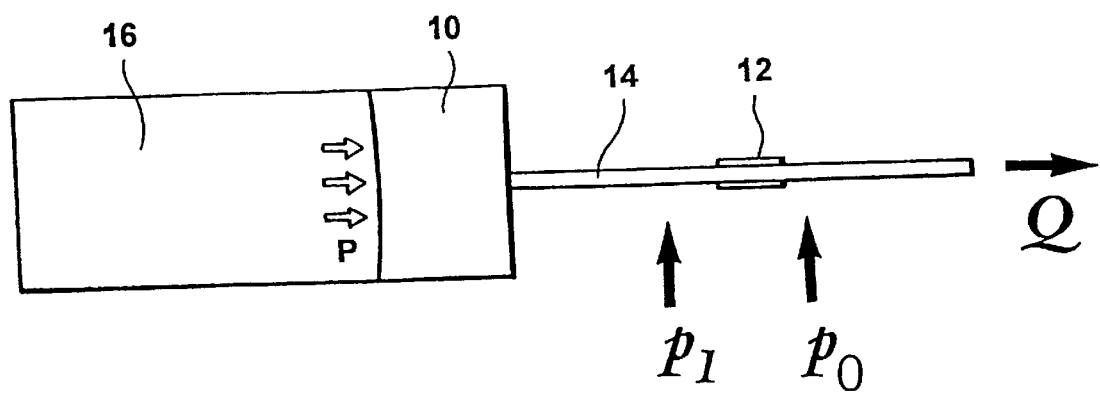
FIG. 8 shows a schematic representation for illustrating the overpressure principle.

In FIGS. 7A and 7B, two further embodiments of flow resistors, which can be used in the system according to the present invention, are shown.

In the embodiment shown in FIG. 7A, two passage openings, an inlet opening 142 and an outlet opening 144, are formed through a substrate 140. The passage openings can be formed in a semiconductor substrate e.g. by carrying out an etching step starting at both main surfaces of said semiconductor substrate, which consists e.g. of silicon. An e.g. V-shaped channel 146, which is in fluid communication with the passage openings, is formed in a main surface of the substrate 140. The main surface of the substrate 140, in which the channel 146 is formed, has again arranged thereon a cover 48. Hence, the channel and the cover define again the flow restriction of the flow resistor. In this embodiment of the flow resistor, the microchannel 146 is arranged on a main surface of the substrate with a depth which is different from that of the passage openings 142 and 144.

FIG. 7B shows a cross-sectional view and a top view of a further embodiment of a micromechanically produced flow resistor which can be used in the system according to the present invention. In contrast to the embodiment of FIG. 7A, one of the passage openings, the outlet opening 158, is, however, arranged in the cover means 56 in the embodiment shown in FIG. 7B. The inlet opening 152 and the channel 154 are formed in a substrate 150 in the same way as in the case of the embodiment shown in FIG. 7A.

It follows that the present invention provides a medicament dosing system which permits the flow rate to be controlled continuously by clocked actuation of a squeezing valve, but which offers an economy-priced throw-away solution, since the squeezing valve does not come into contact with the fluid and is therefore a permanent component.

In addition to controlling the pulse/pause ratio of the squeezing valve, the control device of the medicament dosing system according to the present invention can fulfil further functions on the basis of the temperature measured. It can, for example, be used for administering, in a manner controlled by the patient, an adjustable dose of a medicament, e.g. the bolus administration of an analgesic in an acute case of emergency, by means of the administering device, which can be provided with a bolus key. Furthermore, dosage supervision can be realized, e.g. by observing time limits after the bolus administration so as to prevent a too frequent bolus administration and, consequently, the danger of habit formation. The control unit also permits the number of patient-controlled bolus administrations, current dosing rates and possibly occurring system failures to be recorded so as to obtain additional information on the patient's behaviour. The reading of such data can be carried out e.g. via an integrated data interface. In addition, alarm functions can be implemented, e.g. a warning signal in the case of underdosage or in the case of malfunction of an apparatus. Via the integrated data interface, an arbitrary programmability is additionally available, i.e. arbitrary predetermined values can be programmed for dosing profiles, bolus concentrations and refractory periods.

What is claimed is:

1. A medicament dosing system comprising a replaceable unit and a permanent unit, the replaceable unit comprising:
   a fluid reservoir for receiving therein a pressurizable liquid medicament;
   a temperature sensor for detecting the temperature of said liquid medicament;
   a fluid channel which is provided with a flow resistor and which is in flow communication with the fluid reservoir; and
   a hose means which is connected to the fluid channel; and
the permanent unit comprising:
   a squeezing valve means for squeezing the hose means together; and
   a control means which is coupled to the temperature sensor and the squeezing valve means so as to control a flow rate of the liquid medicament by clocked actuation of said squeezing valve means depending on the temperature detected.

2. A medicament dosing system comprising a replaceable unit and a permanent unit, the replaceable unit comprising:
   a fluid reservoir for receiving therein a pressurizable liquid medicament;
   a fluid channel which is provided with a flow resistor and which is in flow communication with the fluid reservoir; and
   a hose means which is connected to the fluid channel; and
the permanent unit comprising:
   a temperature sensor for detecting the temperature of said liquid medicament;
   a squeezing valve means for squeezing the hose means together; and
   a control means which is coupled to the temperature sensor and the squeezing valve means so as to control a flow rate of the liquid medicament by clocked actuation of said squeezing valve means depending on the temperature detected.

3. A medicament dosing system according to claim 1, comprising in addition a constant pressure transmitter for applying a constant pressure to the liquid medicament before the flow resistor.

4. A medicament dosing system according to claim 1, comprising in addition at least one pressure sensor for detecting the pressure of the liquid medicament before the flow resistor, the at least one pressure sensor being coupled to the control means, and the control means controlling the flow rate of the liquid medicament depending on the temperature detected and the pressure detected.

5. A medicament dosing system according to claim 4, comprising in addition a further pressure sensor for detecting the pressure of the liquid medicament after the flow resistor, said further pressure sensor being coupled to the control means, and said control means controlling the flow rate of the liquid medicament depending on the temperature detected and the difference between the pressures detected.

6. A medicament dosing system according to claim 5, wherein the control means comprises a data interface, an input device and a display device.

7. A medicament dosing system according to claim 1, wherein a filter is arranged between the fluid reservoir and the fluid channel provided with the flow resistor.

8. A medicament dosing system according to claim 1, wherein the flow resistor is formed by means of micromechanical production methods as a micromechanical structure.

9. A medicament dosing system according to claim 7, wherein the temperature sensor and/or the pressure sensors are implemented together with the flow resistor as a micromechanical structure.

10. A medicament dosing system according to claim 8, wherein the micromechanical structure consists of silicon.

11. A medicament dosing system according to claim 2, comprising in addition a constant pressure transmitter for applying a constant pressure to the liquid medicament before the flow resistor.

12. A medicament dosing system according to claim 2, comprising in addition at least one pressure sensor for detecting the pressure of the liquid medicament before the flow resistor, the at least one pressure sensor being coupled to the control means, and the control means controlling the flow rate of the liquid medicament depending on the temperature detected and the pressure detected.

13. A medicament dosing system according to claim 12, comprising in addition a further pressure sensor for detecting the pressure of the liquid medicament after the flow resistor, said further pressure sensor being coupled to the control means, and said control means controlling the flow rate of the liquid medicament depending on the temperature detected and the difference between the pressures detected.

14. A medicament dosing system according to claim 13, wherein the control means comprises a data interface, an input device and a display device.

15. A medicament dosing system according to claim 2, wherein a filter is arranged between the fluid reservoir and the fluid channel provided with the flow resistor.

16. A medicament dosing system according to claim 2, wherein the flow resistor is formed by means of micromechanical production methods as a micromechanical structure.

17. A medicament dosing system according to claim 15, wherein the temperature sensor and/or the pressure sensors are implemented together with the flow resistor as a micromechanical structure.

18. A medicament dosing system according to claim 16, wherein the micromechanical structure consists of silicon.

* * * * *